(12) United States Patent
McFarlane et al.

(10) Patent No.: US 8,643,387 B2
(45) Date of Patent: *Feb. 4, 2014

(54) MOISTURE SENSOR

(71) Applicant: ESI Environmental Sensors Inc., Sidney (CA)

(72) Inventors: Ronald A. McFarlane, Victoria (CA); Basel Zohny, Surrey (CA); Trevor Moat, Victoria (CA)

(73) Assignee: ESI Environmental Sensors Inc., Sidney (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/847,169

(22) Filed: Mar. 19, 2013

(65) Prior Publication Data

US 2013/0214803 A1 Aug. 22, 2013

Related U.S. Application Data

(63) Continuation of application No. 12/745,827, filed as application No. PCT/CA2008/002126 on Dec. 5, 2008, now Pat. No. 8,400,170.

(60) Provisional application No. 61/012,275, filed on Dec. 7, 2007.

(51) Int. Cl.
*G01R 27/26* (2006.01)

(52) U.S. Cl.
USPC .......................................... 324/694; 324/696

(58) Field of Classification Search
USPC .......................................... 324/684, 696, 694
See application file for complete search history.

(56) References Cited

U.S. PATENT DOCUMENTS

2006/0290360 A1* 12/2006 Lee ............................... 324/690

OTHER PUBLICATIONS

U.S. Appl. No. 12/745,827, filed Aug. 18, 2010, now Patent No. 8,400,170. Title: Moisture Sensor, Inventors: McFarlane et al.

* cited by examiner

*Primary Examiner* — Vincent Q Nguyen
(74) *Attorney, Agent, or Firm* — Perry + Currier Inc.; Kristjan Spence

(57) ABSTRACT

A novel and useful sensor and sensing system employs a transmission electrode which provides a length of transmission electrode that is greater than the physical length of the sensor, allowing for the effective and accurate determination of the moisture content of a volume of material using high-frequency measurement methods. The construction of the sensor allows the sensor to be directly inserted into the material, without requiring excavation or backfilling of the sensors in the material. The sensor can be employed as part of a sensing system, with one or more sensors preferably being managed by a field node, which in turn, interoperates with a system master node.

18 Claims, 11 Drawing Sheets

MOISTURE SENSOR

FIELD OF THE INVENTION

The present invention relates to a sensor. More specifically, the present invention relates to a sensor for determining at least the moisture content of soil or other materials in which the sensor is located.

BACKGROUND OF THE INVENTION

With the increase in the expenses associated with irrigation, especially in the cost of obtaining and supplying irrigation water to commercial crops, determining the moisture content of soil has become increasingly important. Various methods are known for determining the amount of moisture present in soil and such systems can include conductivity sensors and time domain transmissiometry (TDT) sensors amongst others.

Conductivity sensors suffer from a lack of precision/sensitivity in their measurements, they must be in electrical contact with the soil and they are not well suited to measuring low levels of moisture and thus they are not generally an acceptable solution.

TDT sensors are better able to accurately measure low moisture levels but, as the sensors must have relatively long sensor transmission lines/electrodes to produce accurate results, such sensors can be difficult to place in the soil.

Typically, holes must be excavated in the soil to receive TDT sensors and then the soil is backfilled around the sensor and/or sensor transmission electrodes. The need to excavate and backfill the soil increases the costs of installing TDT sensors and also results in the soil surrounding the sensor having different characteristics, i.e.—density, etc. than the bulk of the soil. Such different soil characteristics surrounding the sensors can result in less correct readings of soil characteristics.

Further, due to the need for long sensor transmission electrodes, TDT sensors provide measurements over a relatively large volume of soil provide which may be undesired in some circumstances.

Another known soil sensor is disclosed in U.S. Pat. No. 6,441,622 to Wrzesinski et al. which teaches a time domain reflectometry (TDR) soil sensor which employs a coiled sensor transmission electrode that is encircled by a cylindrical secondary electrode. The sensor is installed in the ground with the soil to be tested being received in the space between the secondary electrode and the coiled sensor electrode. As is apparent, the Wrzesinski sensor requires the sensor to be installed by excavation and backfilling of soil about and in the sensor.

SUMMARY OF THE INVENTION

It is an object of the present invention to provide a novel sensor which obviates or mitigates at least one disadvantage of the prior art.

According to a first aspect of the present invention, there is provided a sensor for sensing the moisture content of a volume of material surrounding the sensor, the sensor comprising: an electric circuit board having an electrical circuit employing time domain transmissometry to measure the moisture content of material surrounding a signal transmission electrode connected to the electrical circuit, the electrical length of the signal transmission electrode being greater than the physical length of the circuit board; a sensor body encapsulating the electrical circuit board, the portion of the sensor body contacting the electrical circuit board being formed of a non conductive dielectric material, the sensor body having a first end to be inserted into material to be sensed and a second end, opposite the first end, operable to receive a force to drive the sensor body into the material.

Preferably, the signal transmission electrode is a composite electrode formed from a plurality of serially connected conductive segments on alternating sides of the circuit board. Also preferably, the sensor body is formed by moldings about the electric circuit board.

According to a second aspect of the present invention, there is provided a sensor for sensing the moisture content of a volume of material surrounding the sensor, the sensor comprising: at least two electric circuits, each electronic circuit employing time domain measurement methods to measure the moisture content of material surrounding a signal transmission electrode connected to the electrical circuit, the electrical path length of the signal transmission electrode in each circuit being greater than the overall physical length of the circuit; a sensor body encapsulating each of the electrical circuits which are arranged in a substantially linear manner along the length of the sensor body, the portion of the sensor body contacting the electrical circuits being formed of a non conductive dielectric material, the sensor body having a first end to be inserted into material to be sensed and a second end, opposite the first end, operable to receive a force to drive the sensor body into the material; and wherein each respective one of the at least two electric circuits measures the moisture content of the volume of material adjacent the respective electric circuit.

Preferably, each electric circuit further comprises a second moisture sensor to provide a second determination of the moisture content of material adjacent the electric circuit. Also preferably, the second moisture sensor measures the moisture content of a smaller volume of the material adjacent the electric circuit board than the time domain transmissometry circuit.

Preferably, the signal transmission electrode is a composite electrode formed from a plurality of serially connected conductive segments located on alternating sides of the circuit board.

A further aspect of the specification provides a sensor for sensing the moisture content of a volume of material surrounding the sensor, the sensor including an electrical circuit for implementing a high frequency method for measuring moisture content, the electrical circuit having a signal transmission electrode connected thereto; a mounting substrate supporting the electrical circuit; the signal transmission electrode having an electrical length greater than a physical length of the mounting substrate; and a sensor body encapsulating the mounting substrate and the electrical circuit, at least the portion of the sensor body contacting the electrical circuit being non-conductive.

A still further aspect of the specification provides a sensor for sensing the moisture content of a volume of material surrounding the sensor, the sensor including a plurality of electrical circuits, each electrical circuit for implementing a high frequency method for measuring moisture content, each electrical circuit having a signal transmission electrode connected thereto; a plurality of mounting substrates, each mounting substrate corresponding to and supporting a different one of the plurality of electrical circuits; each signal transmission electrode having an electrical length greater than a physical length of each corresponding one of the plurality of mounting substrates; and a sensor body encapsulating the plurality of mounting substrates and the plurality of electrical circuits, at least the portions of the sensor body contacting the plurality of electrical circuits being non-conductive; wherein each one of the plurality of electrical circuits is operable to measure the moisture content of a volume of material adjacent to the corresponding one of the plurality of mounting substrates.

The present invention provides a sensor and sensing system. The sensors of the present invention employ a novel composite transmission electrode which provides a length of transmission electrode which is longer than the length of the sensor, allowing for the effective and accurate determination of the moisture content of a volume of the material adjacent the sensor using high-frequency measurement methods. The construction of the sensor allows the sensor to be directly inserted into the material, without requiring excavation or backfilling of the sensors once they have been installed in the material. The sensor can be employed as part of a sensing system, with one or more sensors preferably being managed by a field node, which in turn, interoperates with a system master node.

BRIEF DESCRIPTION OF THE DRAWINGS

Preferred embodiments of the present invention will now be described, by way of example only, with reference to the attached Figures, wherein.

DETAILED DESCRIPTION OF THE INVENTION

Figure 1:
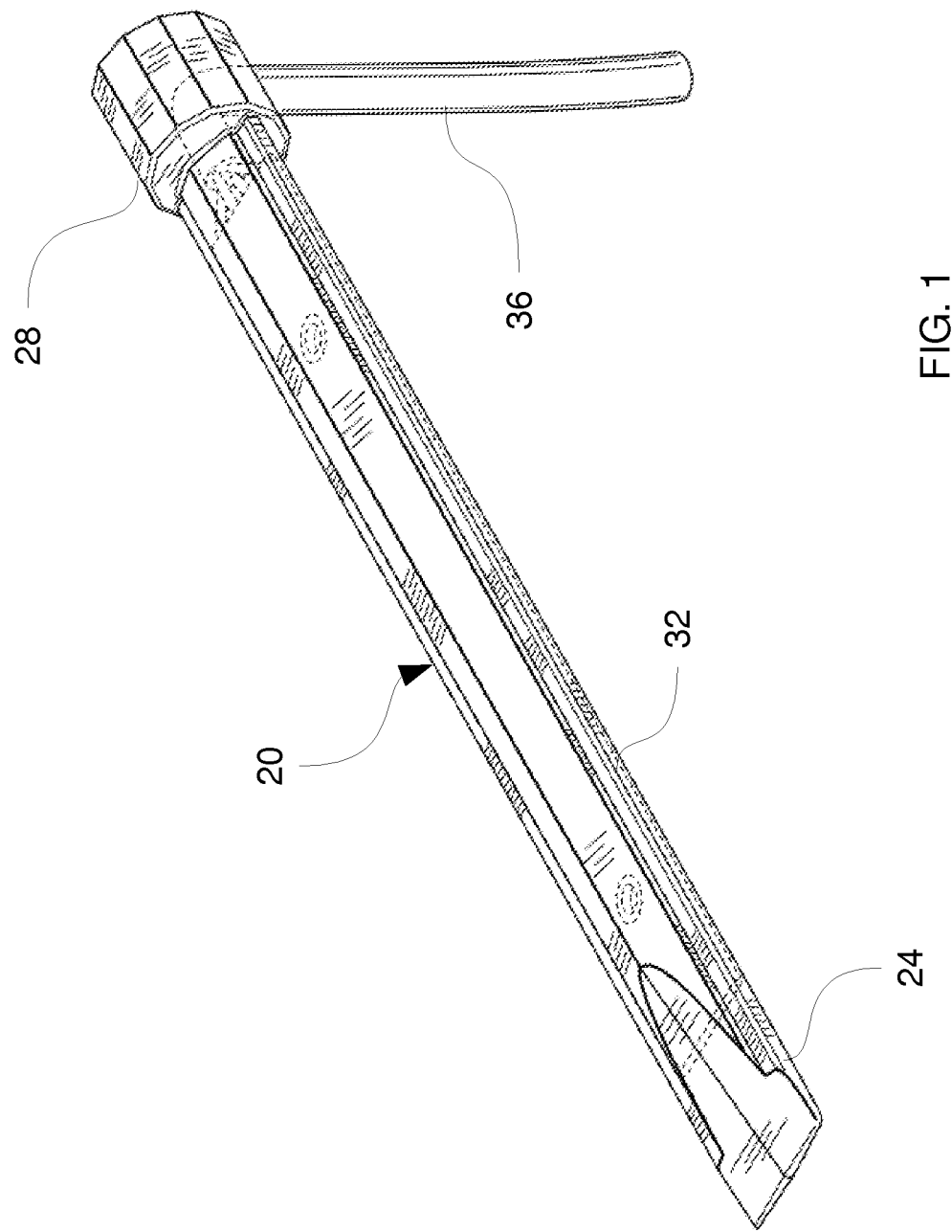
FIG. 1 shows a partially transparent perspective view of a sensor in accordance with the present invention.

In FIG. 1, a sensor in accordance with the present invention is indicated generally at 20. While much of the discussion herein refers to sensing the moisture content of soil, the present invention is not so limited and sensors in accordance with the present invention can be used to determine the moisture content of a wide range of materials including grains, chemical feedstock materials, oil, and petroleum products, etc. Such uses are intended to be within the scope of the present invention.

While the following description discusses TDT technology, other technologies such as time domain reflectometry or other time domain or frequency domain measurement methods can be employed with the present invention, as will be apparent to those with skill in the art. Therefore, the present invention is not limited to the use of TDT technologies.

Sensor 20 includes a main body with a peg-shaped portion 24 and a cylindrical head portion 28. Peg-shaped portion 24 is shaped and sized to allow sensor 20 to be inserted into the soil to be sampled, in a manner similar to a tent peg, by applying force to cylindrical head portion 28, for example with a hammer or other tool, as is described in more detail below.

The TDT circuitry is located on a circuit board 32 which is located within peg-shaped portion 24. Electrical connections 36, including signal leads from the TDT circuitry and the electrical power supply to sensor 20 extend from the outside of sensor 20 through cylindrical head portion 28 and connect to circuit board 32.

Sensor 20 may be assembled by positioning circuit board 32 in a mold, with connectors 36 extending outside of the mold and then filling the mold with a suitable non conductive dielectric material, such as an epoxy, to form sensor 20.

Figure 2:
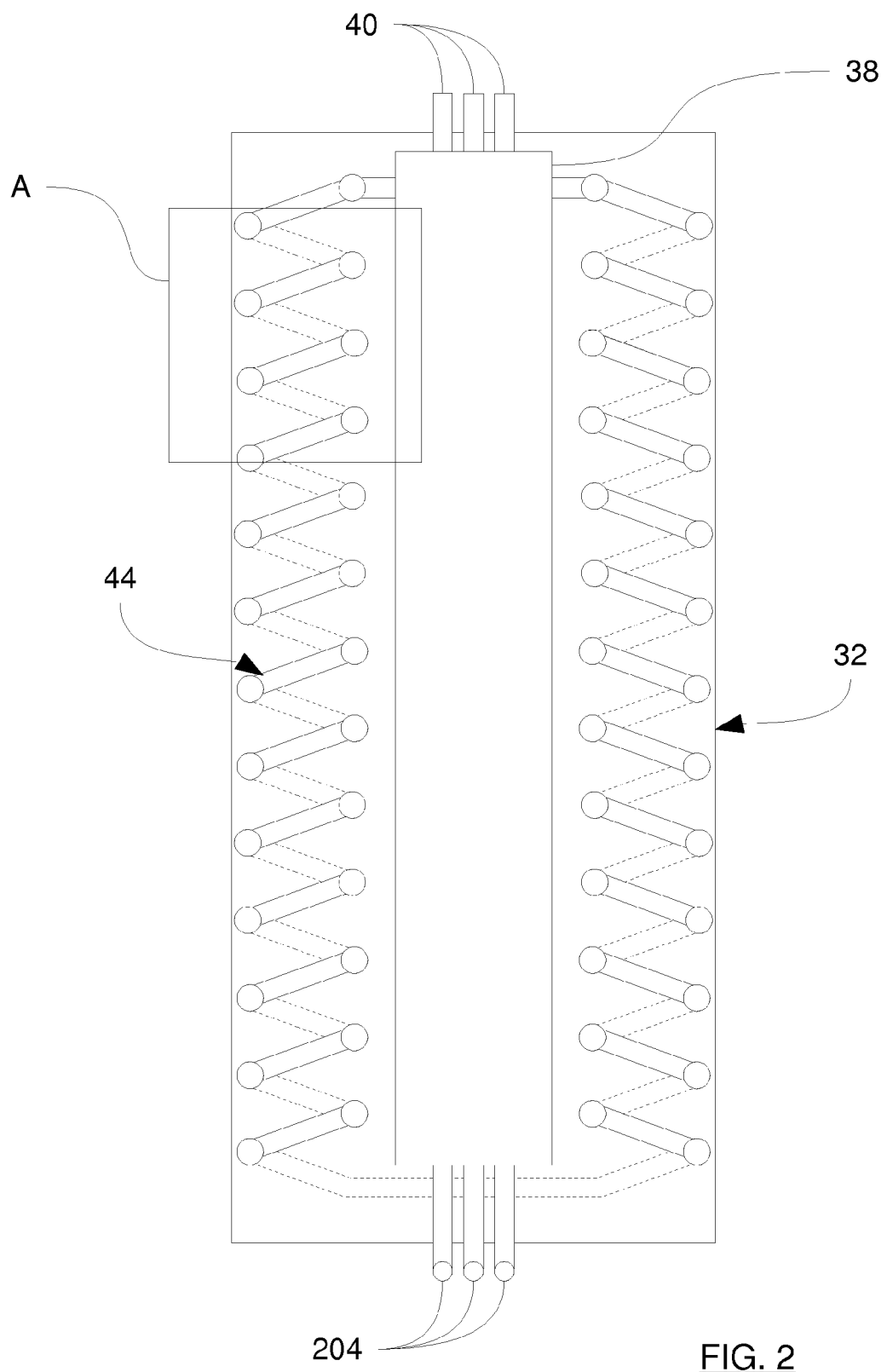
FIG. 2 shows a plan view of a circuit board for use with the sensor of FIG. 1.

Circuit board 32 is shown in more detail in FIG. 2. As shown, circuit board 32 includes a central portion 38 on which the TDT circuitry is installed and a set of connection points 40 to which electrical connections 36 (not shown) are connected.

Figure 3:
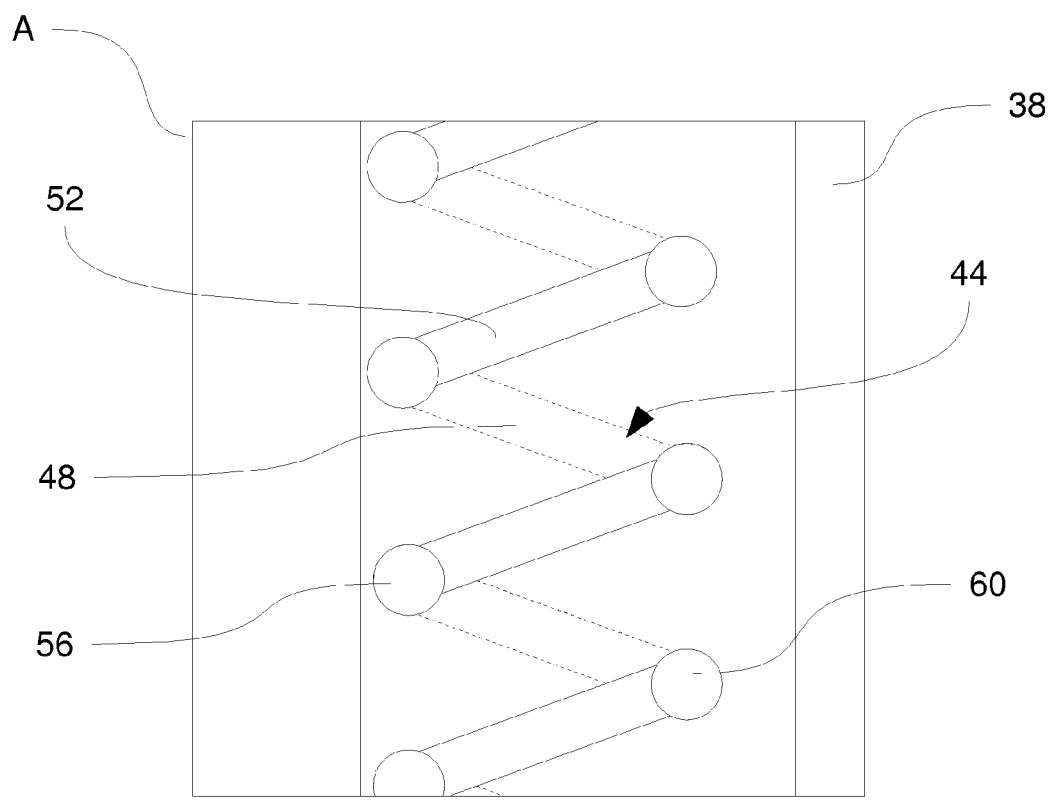
FIG. 3 shows an enlarged view of the region A in FIG. 2.

The signal transmission electrode 44 for the TDT circuitry is located adjacent to each side and along each face of circuit board 32. Preferably, as best shown in FIG. 3, a first set of conductors 48 (shown in dashed lines) are arranged down one face of circuit board 32 and a second set of conductors 52 are arranged down the opposite face of circuit board 32. A first end of each respective one of the first set of conductors 48 is connected by a through-connector or via 56 to a first end of each of a respective one of the second set of conductors 52.

The opposite end of each respective one of the second set of conductors 52 is connected to the opposite end of each respective one of the first set of conductors 48 by another via 60. As should now be apparent, sets of conductors 48 and 52 are thus electrically connected by vias 56 and 60 to form a single, long composite signal transmission electrode 44 which alternates from a conductor in set 48 on the front of circuit board 32 to a conductor in set 52 on the back of circuit board 32 and then back to a conductor in set 48 on the front of circuit board 32, etc.

As shown in FIG. 2, the resulting composite signal transmission electrode 44 extends down one edge of circuit board 32 and then crosses the bottom of circuit board 32 and then extends up the other edge of circuit board 32.

The arrangement of sets of conductors 48 and 52 and vias 56 and 60 result in a signal transmission electrode 44 which occupies a much reduced physical length, in comparison to a linear transmission electrode, while still providing the advantages of the longer transmission electrode, specifically a long length over which signal transmission electrode 44 can interact with the material being measured thus increasing the sensitivity and accuracy of the measurement in comparison to a system using a shorter electrode. In the specific example of FIGS. 2 and 3, circuit board 32 is about eighteen inches long and yet the length of signal transmission electrode 44 for TDT purposes is about six feet.

As should be apparent to those of skill in the art, set of conductors 48 and set of conductors 52, and vias 56 and 60, can all be fabricated using conventional printed circuit board fabrication techniques and thus the manufacturing expense of circuit board 32 is much lower than prior art methods of fabricating transmission signal electrodes. Further, the construction of signal transmission electrode 44 from conductors 48 and 52 affixed to both sides of circuit board 32 allows the effective signal length (required for TDT sensing) of signal transmission electrode 44 to be much longer than the physical length of the sensor.

As will be apparent to those of skill in the art, while constructing composite signal transmission electrode 44 using known printed circuit board manufacturing techniques is presently preferred, the present invention is not limited to such configurations. For example, signal transmission electrode 44 can be fabricated by forming a coil (not shown) of transmission line about a non conductive rod (not shown), or other member, and including this coil in sensor 20.

The reduced physical length achieved with signal transmission electrode 44 provides another advantage in that the volume of soil which sensor 20 senses is related to the physical size of sensor 20, while the accuracy with which this volume is sensed is related to the effective signal length of composite electrode 44. In the above-mentioned specific example of FIG. 2, this means sensor 20 senses the soil about its eighteen inch length with the accuracy of a sensor having a six foot signal transmission electrode length.

Further, circuit board 32 can, if desired, be equipped with additional devices, such as temperature sensing devices, to provide additional information regarding the material surrounding sensor 20.

As mentioned above, another of the advantages of the present invention is the ease with which sensors 20 can be placed in the soil or other material to be sensed. Specifically, in many cases, sensor 20 can be placed by pressing portion 24 into the soil, or other material, by applying force to head portion 28, for example with a hammer, mallet or other suitable tool, such that peg-shaped portion 24 makes intimate contact with undisturbed soil in the areas near the signal transmission electrode 44.

Figure 4:
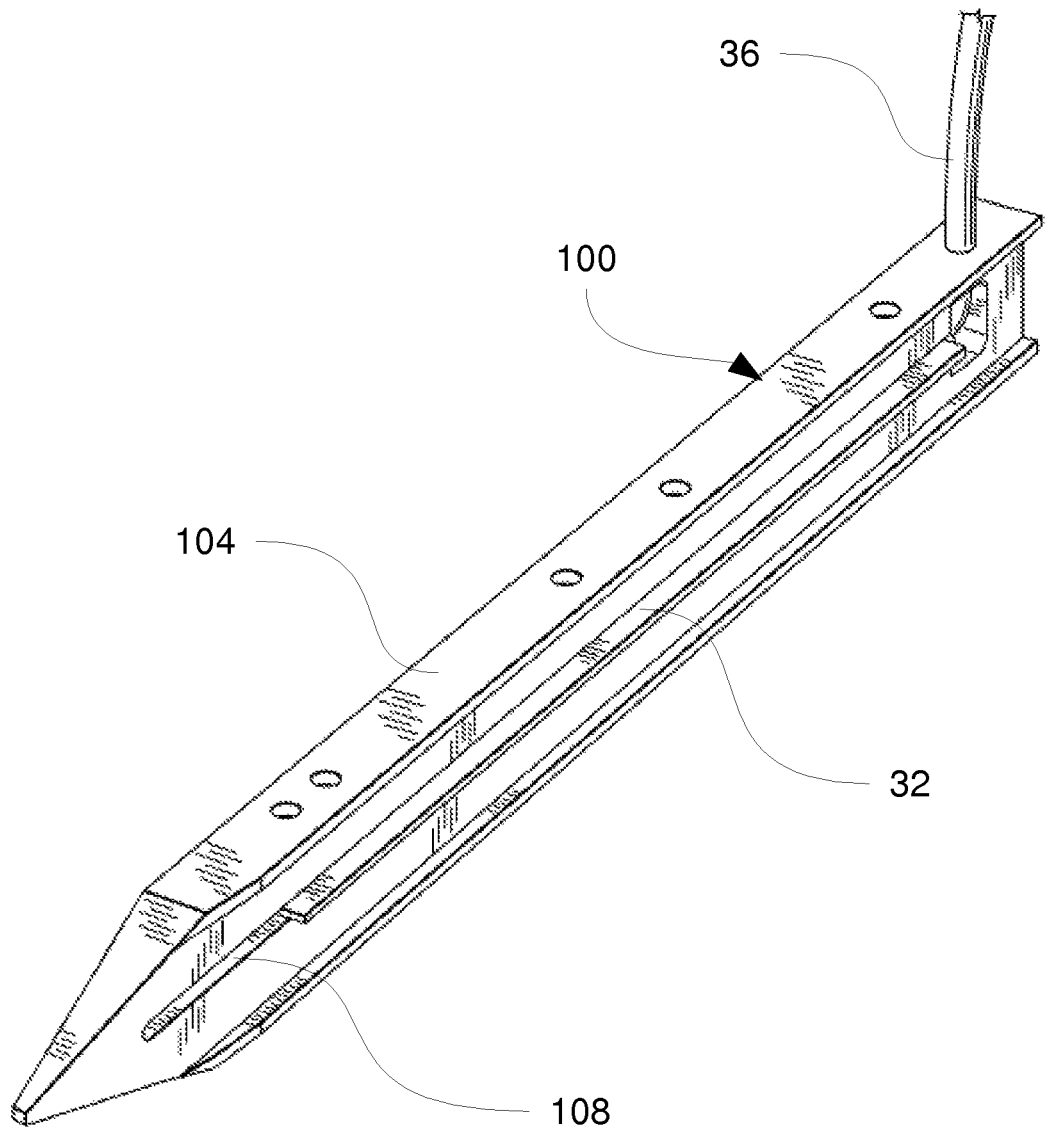
FIG. 4 shows a perspective view of another sensor in accordance with the present invention.
Figure 5:
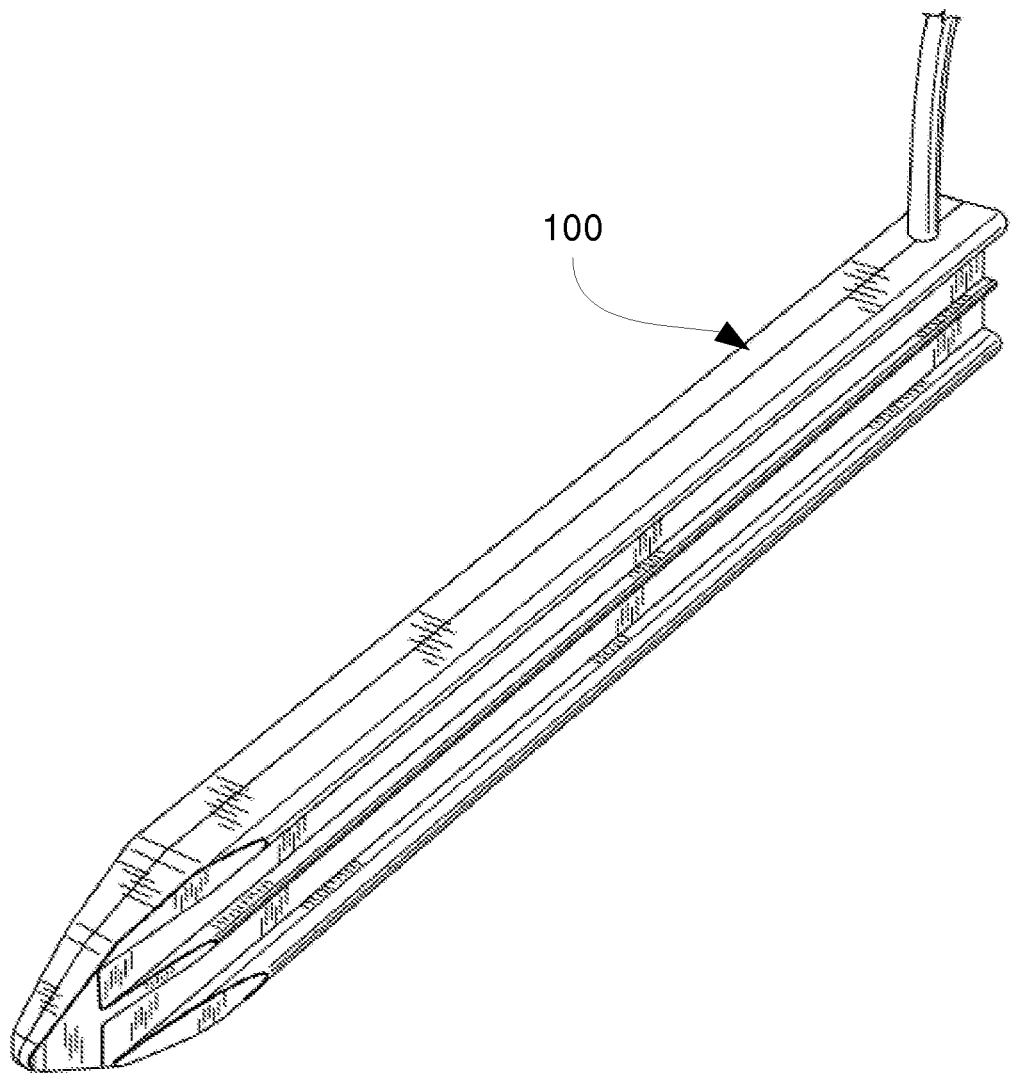
FIG. 5 shows the sensor of FIG. 4 with a protective coating applied to it.

FIG. 4 shows another embodiment of a sensor 100 in accordance with the present invention, wherein like components to those of sensor 20 are indicated with like reference numbers. In this embodiment, sensor 100 comprises a generally peg-shaped body 104 which includes a central slot 108 in which circuit board 32 is received. Body 104 can be formed of extruded metal, or a suitable molded plastic, and once circuit board 32 has been installed and electrical connections 36 properly positioned, sensor 100 can be coated with a protective non conductive dielectric coating, such as an epoxy or urethane coating to inhibit corrosion and to electrically insulate the circuitry on circuit board 32 as well as to affix circuit board 32 in place. FIG. 5 shows sensor 100 after a protective coating has been applied.

Figure 6:
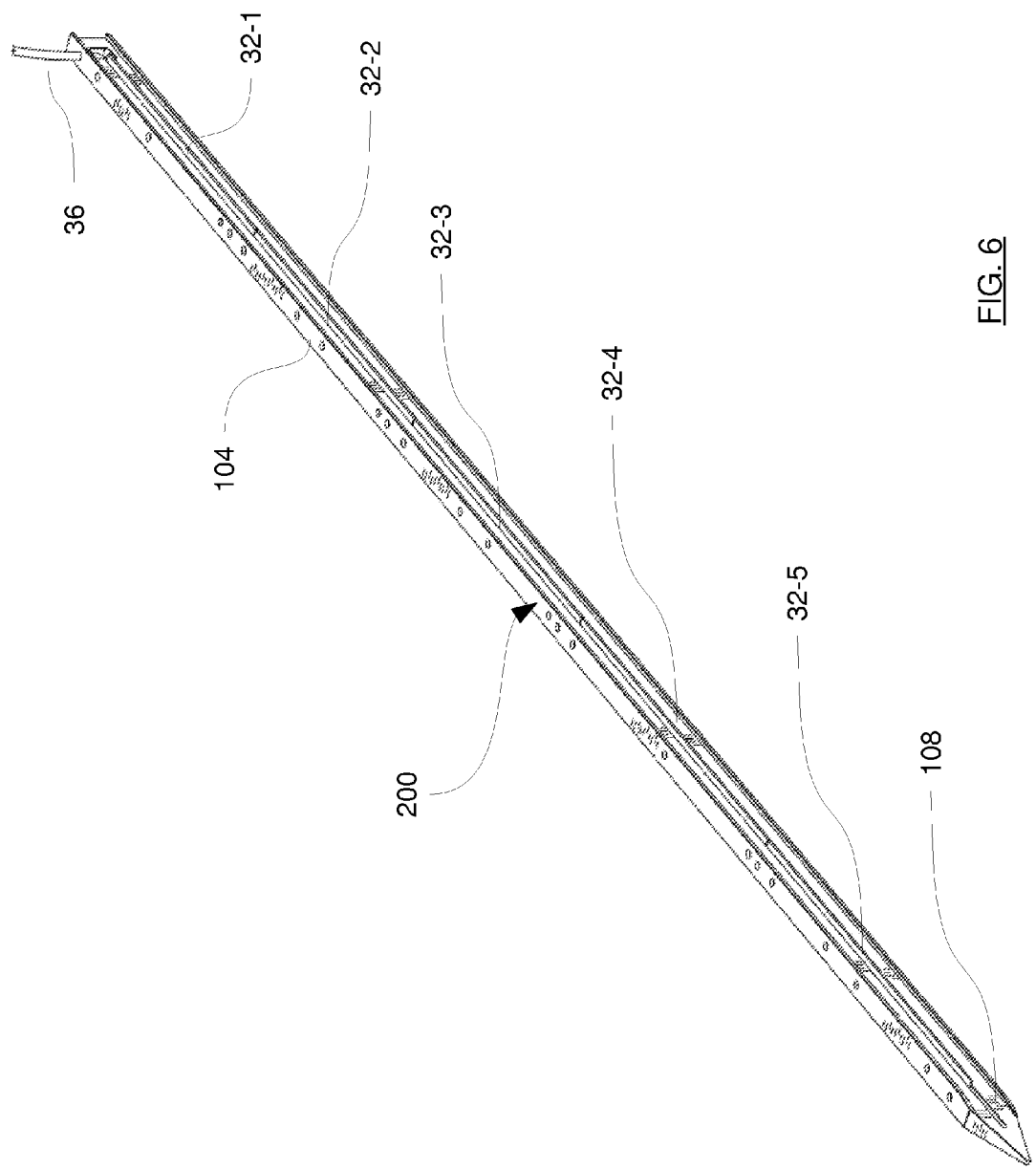
FIG. 6 shows a perspective view of another sensor in accordance with the present invention.

FIG. 6 shows another embodiment of a sensor 200, in accordance with the present invention, wherein like components to those of sensors 20 and 100 are indicated with like reference numbers. As shown, with sensor 200 body 104 is longer than in sensor 100 and central slot 108 is correspondingly long. As is also illustrated, central slot 108 has a circuit board 32-1, circuit board 32-2, circuit board 32-3, circuit board 32-4 and circuit board 32-5 inserted into it.

The electrical power and signal connectors for each circuit board 32-2, 32-3, 32-4 and 32-5 are connected to connectors 204 (best seen in FIG. 2) of the respective circuit board above. Each respective circuit board 32 provides a bus pass-through (not shown) from connectors 204 to connection points 40 and, eventually to connection points 40 on circuit board 32-1 to which electrical connections 36 are connected. Once sensor 200 is assembled, it can be coated, as before, with a suitable protective coating.

As described above, the arrangement of the composite transmission electrode on circuit board 32 allows for the accurate measurement of moisture in the volume of soil surrounding circuit board 32. In sensor 200, multiple circuit boards 32-1, 32-2, 32-3, 32-4 and 32-5 have been placed in the sensor to allow sensor 200 to provide information on a corresponding number of soil volumes along the length of sensor 200. In this manner, sensor 200 can provide a signal representative of the moisture content of the volume of soil adjacent circuit board 32-1, another signal representative of the moisture content of the volume of soil adjacent circuit board 32-2, yet another signal representative of the moisture content of the volume of soil adjacent circuit board 32-3, yet another signal representative of the moisture content of the volume of soil adjacent circuit board 32-4 and yet another signal representative of the moisture content of the volume of soil adjacent circuit board 32-5. In this manner, a user can determine a profile of the moisture content of the soil along the length of sensor 200.

While FIG. 6 shows sensor 200 as having five instances of circuit board 32, the present invention is not limited to this configuration and sensor 200 can include two, three, four, six or virtually any number of instances of circuit board 32 as may be desired.

If desired, circuit boards 32 for sensors 100 or 200 can further include one or more second moisture sensors. Examples of such second moisture sensors can include, without limitation, capacitive sensors, conductivity sensors, or Time Domain Transmissometry or Reflectometry sensors.

These second sensors are arranged to provide their output signals through electrical connections 36 and these second moisture sensors operate with a sensing modality that operates over a small sensing volume, relative to a TDT sensor, immediately adjacent the location of the second sensor. As will be apparent from the discussion below, these second sensors need not provide a high degree of accuracy in their measurements and thus inexpensive implementations can be employed for these second sensors.

Accordingly, a sensor 100 or 200 equipped with circuit boards 32 and which includes a second sensor can, using the TDT sensing circuitry, provide an accurate measurement of the moisture content of the volume of soil adjacent each circuit board 32 but can also provide information from the second sensors relating to a determination of the moisture immediately adjacent the second sensor location. Thus, sensors 100 or 200 which are also equipped with these additional second sensors can provide an indication of the rate at which water is penetrating the soil, which is referred to herein as the "wetting front". An indication of the propagation of the wetting front through soil can provide another useful measure for controlling an irrigation system.

Figure 7:
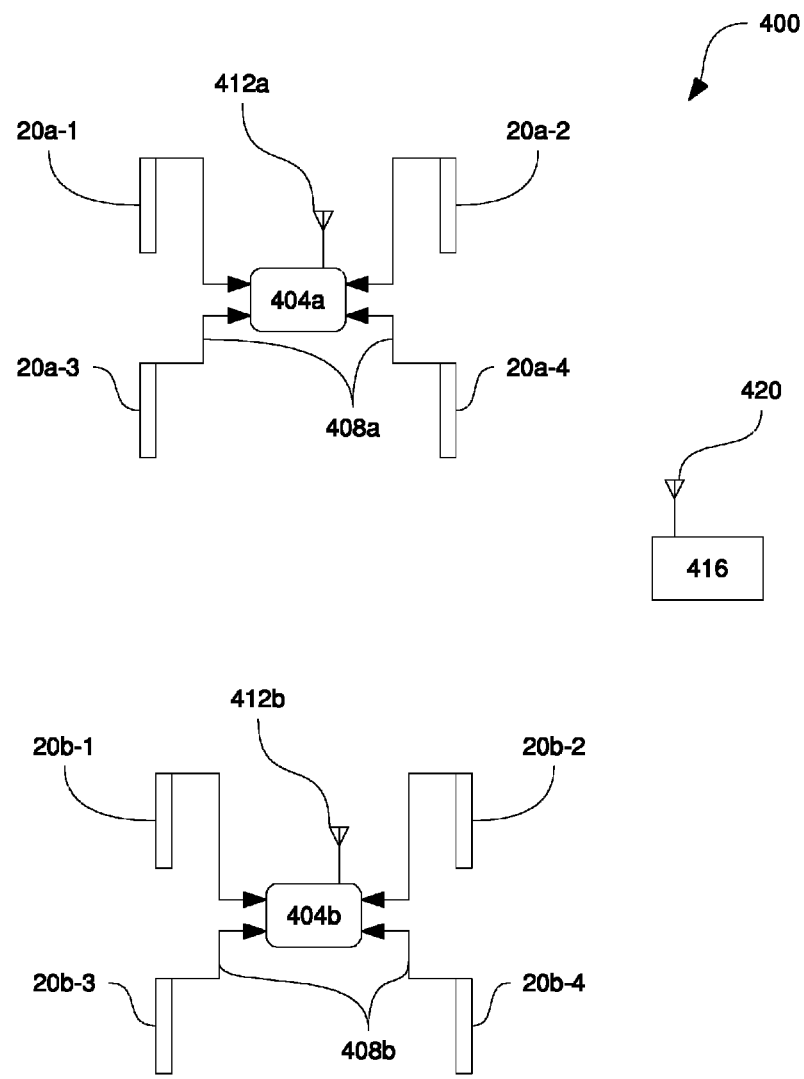
FIG. 7 shows a schematic representation of a sensor system in accordance with the present invention.

A sensing system 400, in accordance with the present invention, is shown in FIG. 7. System 400 includes a variety of sensors in accordance with the present invention and in the illustrated embodiment these are sensors 20. However, as will be apparent to those of skill in the art, sensors 100 or sensors 200 can be employed and/or sensors 20, 100 and 200 can be combined within system 400 if desired.

Each sensor 20 is connected to a field node 404 via a suitable connection 408 and the connected field node 404 manages the sensors to which it is connected. A field node 404 and the set of sensors 20 which it manages are referred to herein as a cell. It is presently preferred that field nodes 404a and 404b provide power to each of sensors 20a-1 to 20a-4 and 20b-1 to 20b-4 respectively which they manage, and receive the sensor signals from each of sensors 20a-1 to 20a-4 and 20b-1 to 20b-4 respectively which they manage. Thus, in a presently preferred embodiment, connections 408a and 408b are cabled connections. However, it is also contemplated that, in some cases, it may be desired that each sensor 20 include its own power source and include a radio transmitter to forward its sensor signals via a radio signal and such a configuration is intended to be within the scope of the present invention.

Each field node 404 can manage one or more sensors 20 and preferably includes a robust means for powering those sensors 20. In a present embodiment, field nodes 404 include a set of solar cells and a rechargeable battery system (not shown) which provides power to field node 404 and each sensor 20 it manages. However, it is also contemplated that field node 404 can be connected to an external power source, such as a 120 VAC power supply or other suitable power supply which may be available, or can be powered by an appropriate set of disposable batteries, etc. if desired.

In addition to preferably including a power source for sensors 20, field node 404 includes a processing means, such as a suitable 8 bit or 16 bit microcontroller and a suitable memory such as a FLASH ROM or battery backed up static ROM which are operable to allow field node 404 to receive, process and store signals from sensors 20 indicating the amount of moisture measured by each circuit board 32 in each sensor 20 and/or any other information from circuit boards 32, such as temperature measurements, etc.

Field node 404 further includes a communications means, such as a radio transceiver 412, by which field node 404 can provide the stored signals to a system master node 416 which includes a corresponding radio transceiver 420 and/or by which each field node 404 can receive commands from the system master node 416. In a presently preferred embodiment of the invention, field nodes 404 and system master node 416 communicate via a digital communications system compatible with the IEEE 802.15.4/Zigbee protocols, and the contents of this standard and protocols are included herein, in their entirety, by reference.

System master node 416 can be directly connected to a user, such as by a direct connection to a laptop or personal computer, or can be connected to a remote user via any suitable means, such as a data communications network such as the Internet. System master node 416 can connect to the user or to the data communications network via a physical or wireless data link, as appropriate.

Soil sensing system 400 can be operated in a variety of manners, as may occur to those of skill in the art. For example, field nodes 404 may process and store signals from managed sensors 20 at regular intervals and forward those stored signals to system master node 416 at preset intervals (i.e. hourly, daily, etc.) or on demand. In other embodiments, field nodes 404 can process signals from managed sensors 20 and provide those signals to system master node 416 substantially in real time. A variety of other manners of operating soil sensing system 400 will occur to those of skill in the art.

The present invention provides a novel and useful soil sensor and soil sensing system. The soil sensors of the present invention employ a novel composite transmission electrode which provides a length of transmission electrode which is greater than the length of the sensors, allowing for the effective and accurate determination of the moisture content of a volume of soil using TDT methods. The construction of the soil sensor allows the sensor to be directly inserted into the soil, without requiring excavation or backfilling of the sensors in the soil. The soil sensor can be employed as part of a soil sensing system, with one or more sensors preferably being managed by a field node, which in turn, interoperates with a system master node.

A further non-limiting embodiment will now be described with reference to FIGS. 8-12, in which like components to those of sensor 20 will be indicated with like reference numbers, the reference numbers having the suffix "a."

Figure 8:
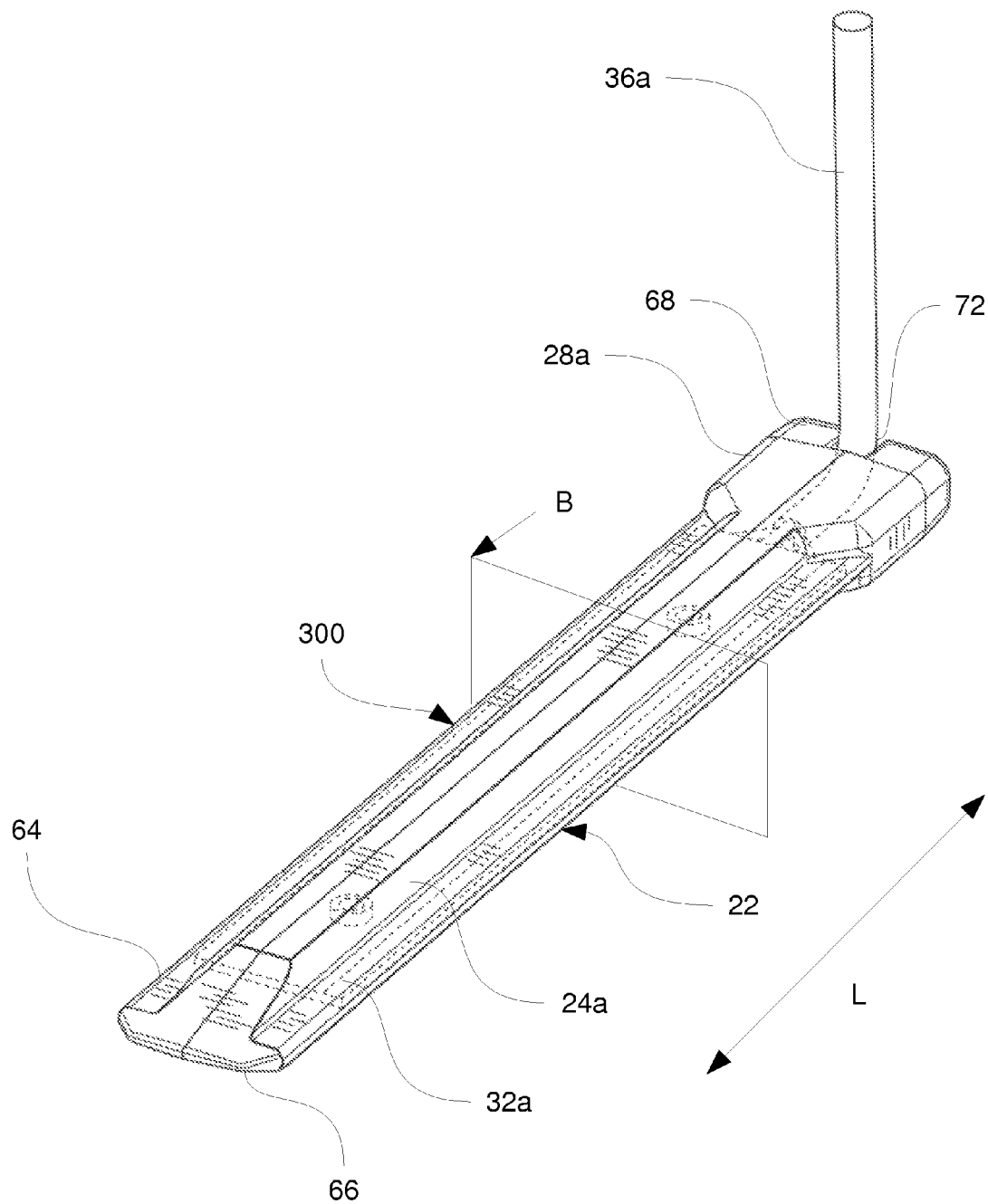
FIG. 8 shows a perspective view of a sensor in accordance with a further non-limiting embodiment.

With reference to FIG. 8, a further non-limiting embodiment of a sensor is indicated generally at 300. Sensor 300 includes a body 22 which in turn includes a chisel-shaped portion 24a and a head portion 28a. An electrical sensing circuit is supported by a mounting substrate 32a (visible in dashed lines in FIG. 8) housed within body 22, and will be described in further detail below. In some non-limiting embodiments as illustrated in FIG. 8, mounting substrate 32a may be housed entirely within chisel-shaped portion 24a. Those skilled in the art will appreciate, however, that mounting substrate 32a may also be housed partly in head portion 28a, for example. Electrical connections 36a extend from outside sensor 300 into head portion 28a to connect to substrate 32a. Electrical connections 36a may be in the form of sheathed cabling, and may include, but are not particularly limited to, signal leads and electrical power supply for sensor 300.

Body 22 of sensor 300 may include separate halves 64 and 66. Sensor 300 may further include a cap 68. Halves 64, 66 and cap 68 may be molded or extruded from metals or from suitable non-conductive materials. As will be understood by those skilled in the art, if metals are used for any of halves 64, 66 and cap 68, mounting substrate 32a may be coated in a non-conductive material before insertion into body 22. For example, body 22 may form a rigid carrier frame of hard plastic or metal, while mounting substrate 32a may be encased in a non-conductive dielectric sheath within body 22.

Figure 9:
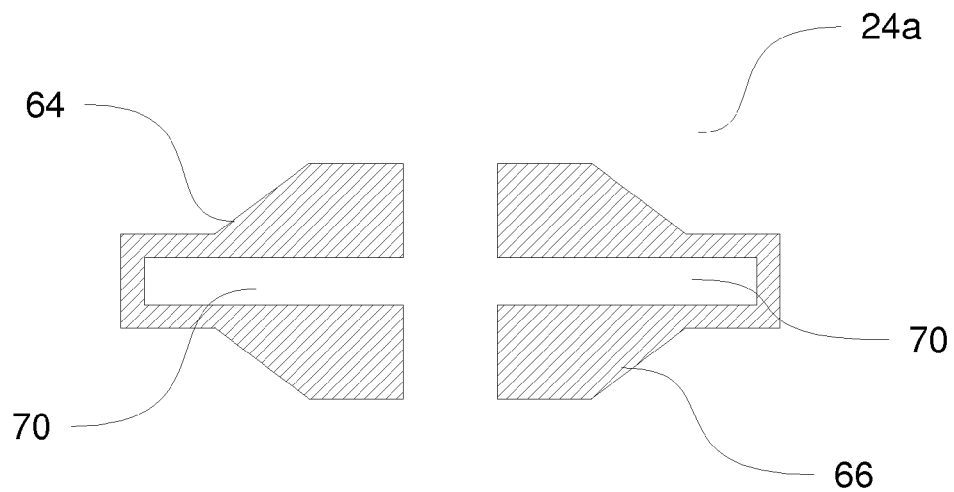
FIG. 9 shows a cross section B of the sensor of FIG. 8, according to a non-limiting embodiment.
Figure 10:
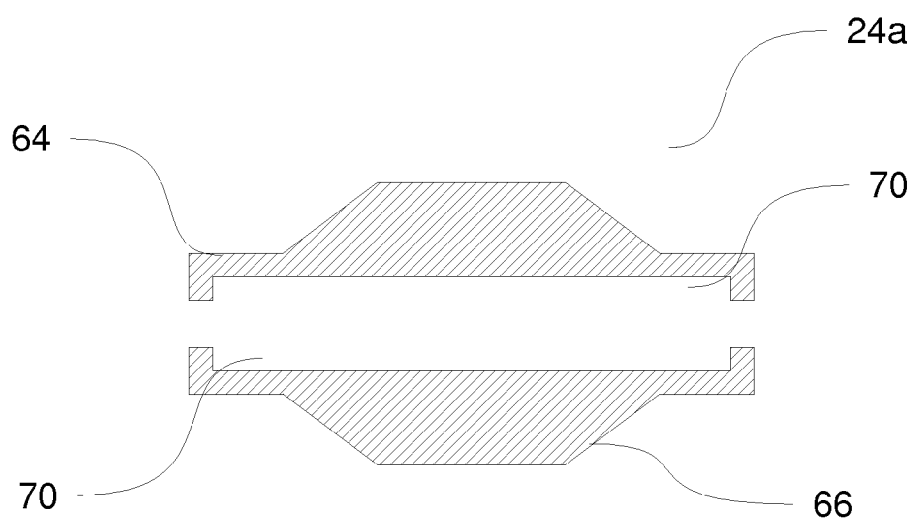
FIG. 10 shows a cross section B of the sensor of FIG. 8, according to another non-limiting embodiment.

Halves 64 and 66 are illustrated in the cross sections of FIGS. 9 and 10, taken at region B of sensor 300. It will be noted that in cross section, chisel-shaped portion 24a preferably has a first dimension which is substantially larger than a second dimension. For example, in FIGS. 9 and 10 chisel-shaped portion 24a is shown as being substantially greater in width than in height. Such a configuration permits, for example when sensor 300 is installed in soil to measure moisture content, sensor 300 to be installed horizontally relative to a ground surface (not shown) without significantly impeding the gravitational flow of water around sensor 300.

FIG. 9 illustrates the division of halves 64 and 66 of body 22 in some non-limiting embodiments. FIG. 10 similarly illustrates the division of halves 64 and 66 in other non-limiting embodiments. It will be clear to those skilled in the art that further configurations of halves 64 and 66 are possible, and are intended to fall within the scope of the specification.

As shown in FIGS. 9 and 10, each of halves 64 and 66 of body 22 may define therein a channel 70 for receiving a portion of mounting substrate 32a (not shown). Channels 70 of halves 64 and 66, when halves 64 and 66 are joined, form a space within body 22 for receiving mounting substrate 32a.

Assembling sensor 300 may be accomplished by joining halves 64 and 66 with a fastener such as an adhesive so as to form body 22a with a space defined therein. The space defined in body 22a may extend to the end of head portion 28a, thus providing an opening at head portion 28a into which mounting substrate 32a may then be inserted by sliding. In other non-limiting embodiments, the space within body 22a may not extend to the end of head portion 28a, and mounting substrate 32a may instead be received, at least in part, in a channel 70 before halves 64 and 66 are joined. It will be understood that once mounting substrate 32a is housed within body 22 of sensor 300, connections 36a may be coupled to mounting substrate 32a.

Once halves 64 and 66 are joined and mounting substrate 32a is inserted into the space via an opening at head portion 28a, any remaining volume of the space in body 22 may be potted with a filler material. The filler material may be, for example, a urethane or epoxy compound, or may also be any other suitable material known to those skilled in the art. Cap 68 may then be coupled to body 22 at head portion 28a as shown in FIG. 8. Cap 68 may be coupled to head portion 28a of body 22 by way of a fastener such as an adhesive.

It will be noted by those skilled in the art that cap 68 permits electrical connections 36a to protrude from sensor 300 at an angle of substantially 90° relative to the length L of body 22 as shown in FIG. 8. It will be clear to those skilled in the art that electrical connections 36a may also protrude from sensor 300 at an angle of substantially 0° or 180° relative to length L, or at an angle intermediate to the above values. In general terms, cap 68 may be structured—for example by provision of a gap 72—to allow electrical connections 36a to protrude from sensor 300 at a wide variety of angles relative to sensor 300.

Mounting substrate 32a of sensor 300 will now be described with reference to FIGS. 11 and 12. In some non-limiting embodiments, mounting substrate 32a may be a printed circuit board (PCB), though it is not intended to be limited to a PCB and may be any of a variety of mounting substrates known to those skilled in the art. Mounting substrate 32a supports an electrical sensing circuit 38a which implements a high frequency method for measuring moisture content. The high frequency measurement method may be based on time domain methods (such as time domain transmissiometry), frequency domain methods or mixed time and frequency domain methods. Mounting substrate 32a may include connectors 40a for connecting to electrical connections 36a, as well as connectors 204a for connecting to further mounting substrates (not shown).

Mounting substrate 32a may also support a signal transmission electrode 44a. In the embodiment depicted, the signal transmission electrode extends along each edge of each face of mounting substrate 32a, and is connected to electrical circuit 38a. Signal transmission electrode 44a includes a first set of conductors 48a (shown in dashed lines in FIG. 11) arranged down one face of mounting substrate 32a and a second set of conductors 52a arranged down the opposite face of mounting substrate 32a. A first end of each respective conductive segment of the first set of conductors 48a is connected by a through-connector or via 56a to a first end of each respective conductive segment of the second set of conductors 52a. The opposite end of each respective conductive segment of the second set of conductors 52a is connected to the opposite end of each respective conductive segment of the first set of conductors 48a by another via 60a. Sets of conductors 48a and 52a are thus electrically connected by vias 56a and 60a to form a single, long composite signal transmission electrode 44a which alternates from a conductive segment in set 48a on one face of mounting substrate 32a to a conductive segment in set 52a on the opposing face of mounting substrate 32a and then back to a conductive segment in set 48a, and so on.

Figure 11:
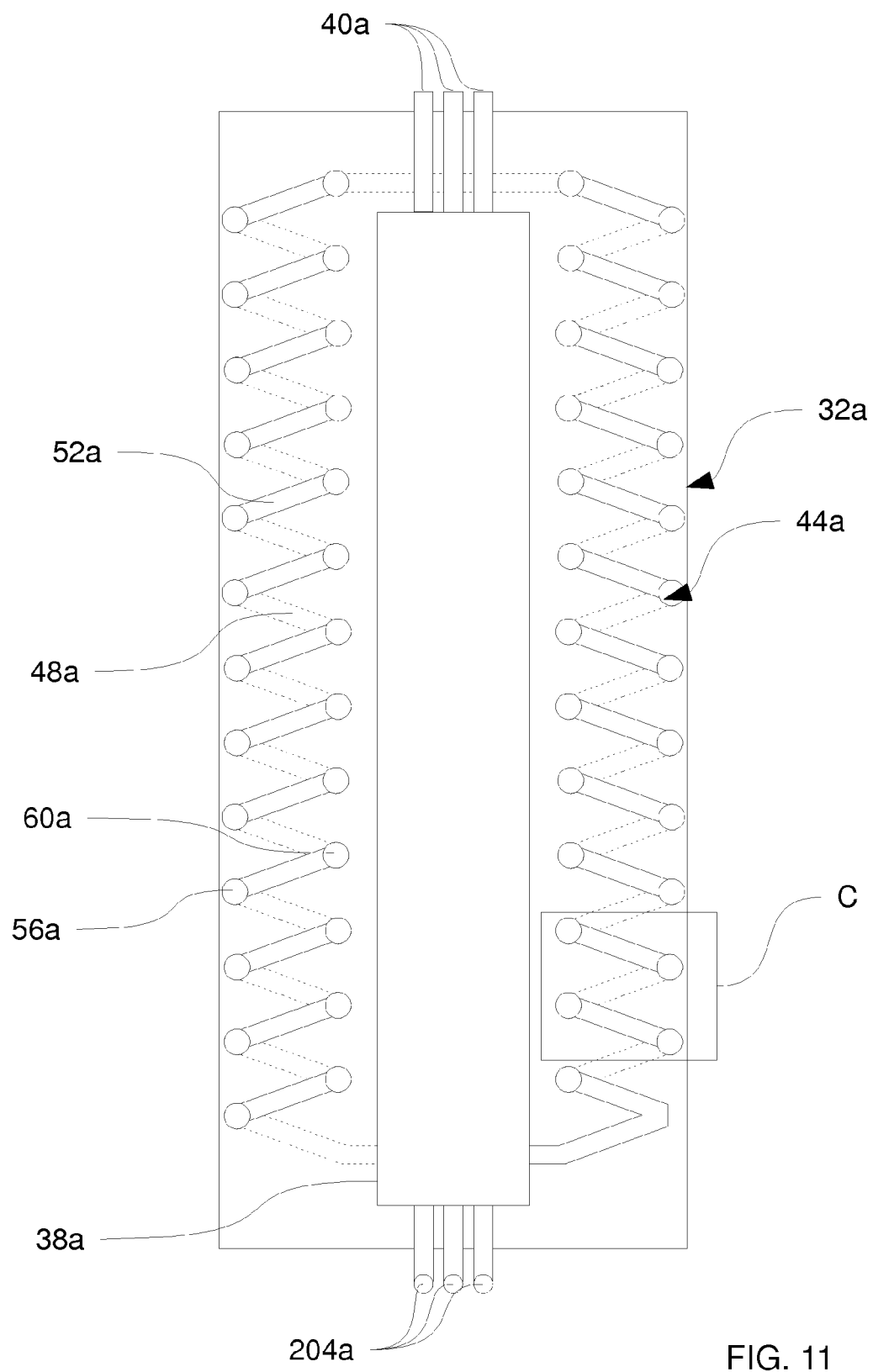
FIG. 11 shows a plan view of a substrate for use with the sensor of FIG. 8.

As best seen in FIG. 11, signal transmission electrode 44a begins at a connection to electrical circuit 38a—the signal transmission electrode input—and runs along one edge of mounting substrate 32a, crosses to the opposing edge of mounting substrate 32a and returns along that edge to reconnect to electrical circuit 38a at a signal transmission electrode output.

Note that the conductive segments in set of conductors 48a are substantially parallel to each other, and that the conductive segments in set of conductors 52a are also substantially parallel to each other. Set of conductors 48a, however, are angled relative to set of conductors 52a such that signal transmission electrode 44a follows a substantially "zig-zag" shaped path. It will be understood that other configurations of signal transmission electrode are also contemplated herein. For example, signal transmission electrode may reside only on one face of mounting substrate 32a, and/or may have a crenellated or serpentine configuration (not shown). Such variations are intended to fall within the scope of the specification.

In general, the contemplated signal transmission electrode 44a may provide an electrical length that is greater than the physical length of mounting substrate 32a. The electrical length provided by signal transmission electrode 44a may further be greater than one or both of twice the length of mounting substrate 32a, and the perimeter of mounting substrate 32a. This arrangement provides a desirable length over which electrical signals may be driven through signal transmission electrode to interact with the material being measured, thus increasing the sensitivity and accuracy of the measurement in comparison to a system using a shorter electrode. In the embodiment depicted in FIG. 11, mounting substrate 32a is about seven inches long, while the electrical length provided by signal transmission electrode 44a is about thirty two inches.

In sensing the moisture content of a volume of material surrounding sensor 300, electrical circuit 38a may be configured to apply one or more electrical pulses to the signal transmission electrode input, and to analyze the response characteristics of the resulting electrical pulses received at the signal transmission electrode output. Alternatively, electrical circuit 38a may be configured to apply one or more sinusoidal electrical signals to the signal transmission electrode input, and to analyze at least one of the magnitude and phase characteristics of the resulting sinusoidal electrical signals received at the signal transmission electrode output.

Figure 12:
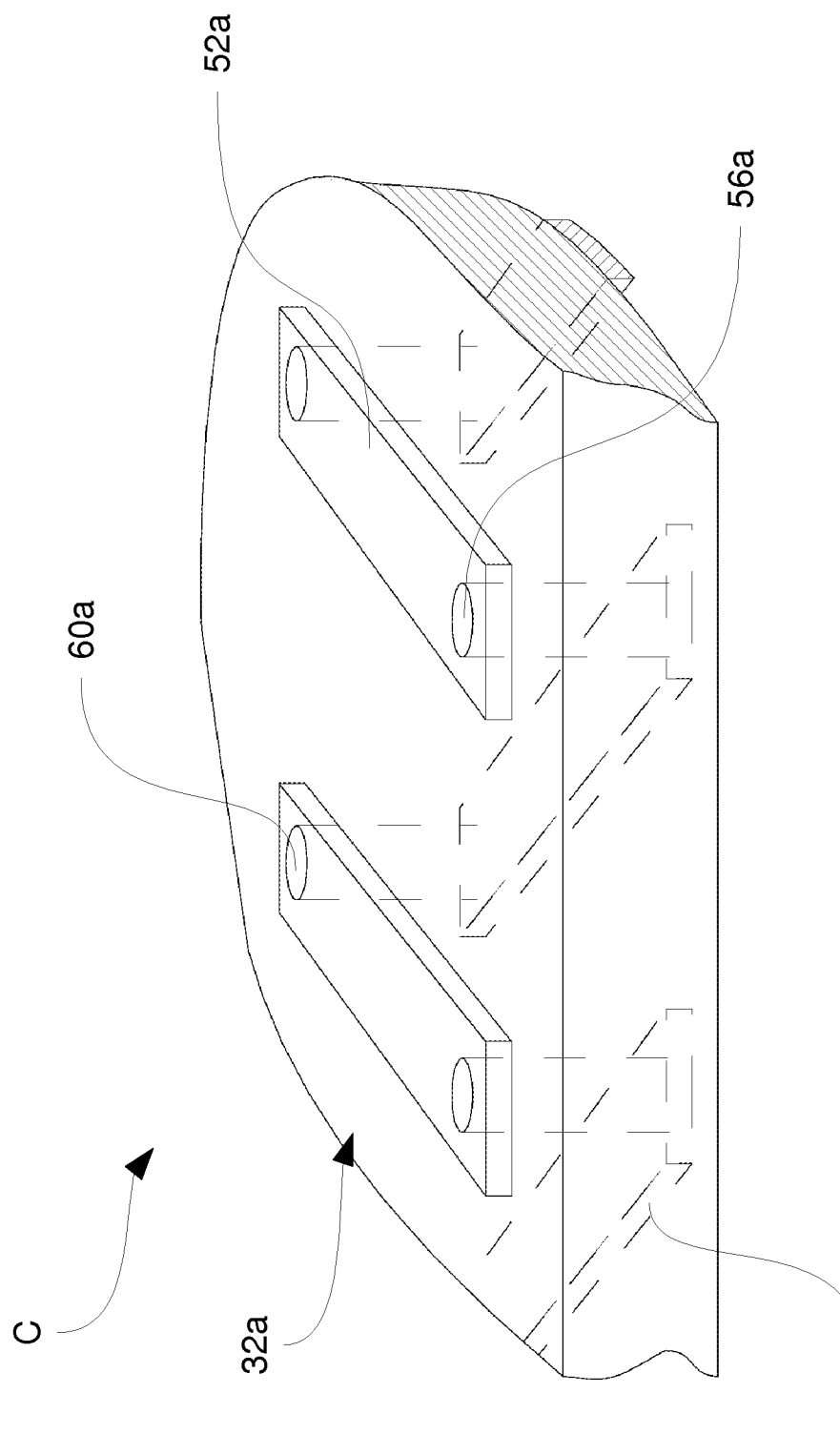
FIG. 12 shows a partial section of region C of the substrate of FIG. 11.

FIG. 12 depicts a partial section view of region C indicated in FIG. 11, illustrating first and second sets of conductors 48a and 52a on respective opposing faces of mounting substrate 32a, connected through mounting substrate 32a by vias 56a and 60a.

Mounting substrate 32a may also, if desired, support additional devices and features to provide additional information regarding the material surrounding sensor 300. For example, mounting substrate 32a may support a temperature sensor (not shown) which allows for compensation of moisture content measurements due to variations in soil temperature. As a further example, electrical circuit 38a may also be configured to measure the attenuation of high-frequency components in a signal, allowing a determination of the bulk conductivity of the material proximal to signal transmission electrode 44a. As will be appreciated by those of skill in the art, measurements of bulk conductivity may be used to adjust moisture content measurements for greater accuracy.

Returning to FIGS. 9 and 10, it will be noted that the walls of body 22 of sensor 300 are thinner in the peripheral areas where the edges of mounting substrate 32a will be received than in the central area where electrical circuit 38a will be received.

Sensor 300 may be installed, for example, by making a primer hole in the material to be tested similar in shape to sensor 300, and press-fitting sensor 300 into the primer hole. It will be appreciated by those skilled in the art that sensor 300 may also be installed as described above in connection with sensor 20, by applying force to head portion 28a to drive chisel-shaped portion 24a into the material to be tested.

Sensor 300 may also include a plurality of electrical circuits 38a supported by a plurality of corresponding mounting substrates 32a, similarly to sensor 200 described above with reference to FIG. 6. The mounting substrates 32a may be substantially coplanar with each other, and arranged substantially lengthwise within a suitably extended sensor body. Sensor 300 may also be used, alone or in conjunction with sensors 20, 200, in a system similar to system 400, as described above with reference to FIG. 7.

The above-described embodiments of the invention are intended to be examples of the present invention and alterations and modifications may be effected thereto, by those of skill in the art, without departing from the scope of the invention which is defined solely by the claims appended hereto.

We claim:

1. A sensor for sensing the moisture content of a volume of material surrounding the sensor, the sensor comprising:
   an electrical circuit for implementing a high frequency method for measuring moisture content, the electrical circuit having a signal transmission electrode connected thereto, the electrical circuit being configured to apply one or more electrical pulses to an input of the signal transmission electrode, and further being configured to analyze the response characteristics of the one or more electrical pulses received at an output of the signal transmission electrode;
   a mounting substrate supporting the electrical circuit and the signal transmission electrode;
   the signal transmission electrode having an electrical length greater than a physical length of the mounting substrate; and
   a sensor body encapsulating the mounting substrate and the electrical circuit, at least a portion of the sensor body contacting the electrical circuit being non-conductive.

2. The sensor of claim 1, wherein the length of the signal transmission electrode is greater than twice the physical length of the mounting substrate.

3. The sensor of claim 2, wherein the length of the signal transmission electrode is greater than a physical perimeter of the mounting substrate.

4. The sensor of claim 1, wherein the mounting substrate is a printed circuit board, and wherein the signal transmission electrode is a composite electrode comprising a plurality of serially connected conductive segments located on alternating sides of the printed circuit board, each of the plurality of serially connected conductive segments being connected to the subsequent one of the plurality of serially connected conductive segments by a conductive via extending between opposing sides of the printed circuit board.

5. The sensor of claim 1, the sensor body comprising a rigid carrier frame and a non-conductive dielectric sheath about the mounting substrate and the electrical circuit.

6. The sensor of claim 1, wherein the sensor body comprises a first tapered end for facilitating insertion into the material to be sensed.

7. The sensor of claim 1, wherein the sensor body comprises a second end opposite the first end for receiving a force to drive the sensor body into the material to be sensed.

8. The sensor of claim 1, further comprising:
   a cap coupled to the sensor body;
   electrical connections protruding from the cap for supplying electrical power to the sensor;
   the cap being configured to permit the cable to protrude at an angle between zero and ninety degrees with respect to a length of the sensor.

9. The sensor of claim 1, further comprising, encapsulated by the sensor body:
   one or more additional electrical circuits, each connected to a different one of one or more additional signal transmission electrodes; and
   one or more additional mounting substrates, each supporting a different one of the one or more additional electrical circuits and a different one of the one or more additional signal transmission electrodes.

10. A sensor for sensing the moisture content of a volume of material surrounding the sensor, the sensor comprising:
    an electrical circuit for implementing a high frequency method for measuring moisture content, the electrical circuit having a signal transmission electrode connected thereto, the electrical circuit being configured to apply one or more sinusoidal electrical signals to an input of the signal transmission electrode, and further being configured to analyze at least one of the magnitude and phase characteristics of the one or more sinusoidal electrical signals received at an output of the signal transmission electrode;
    a mounting substrate supporting the electrical circuit and the signal transmission electrode;
    the signal transmission electrode having an electrical length greater than a physical length of the mounting substrate; and
    a sensor body encapsulating the mounting substrate and the electrical circuit, at least a portion of the sensor body contacting the electrical circuit being non-conductive.

11. The sensor of claim 10, wherein the length of the signal transmission electrode is greater than twice the physical length of the mounting substrate.

12. The sensor of claim 11, wherein the length of the signal transmission electrode is greater than a physical perimeter of the mounting substrate.

13. The sensor of claim 10, wherein the mounting substrate is a printed circuit board, and wherein the signal transmission electrode is a composite electrode comprising a plurality of serially connected conductive segments located on alternating sides of the printed circuit board, each of the plurality of serially connected conductive segments being connected to the subsequent one of the plurality of serially connected conductive segments by a conductive via extending between opposing sides of the printed circuit board.

14. The sensor of claim 10, the sensor body comprising a rigid carrier frame and a non-conductive dielectric sheath about the mounting substrate and the electrical circuit.

15. The sensor of claim 10, wherein the sensor body comprises a first tapered end for facilitating insertion into the material to be sensed.

16. The sensor of claim 10, wherein the sensor body comprises a second end opposite the first end for receiving a force to drive the sensor body into the material to be sensed.

17. The sensor of claim 10, further comprising:
    a cap coupled to the sensor body;
    electrical connections protruding from the cap for supplying electrical power to the sensor;
    the cap being configured to permit the cable to protrude at an angle between zero and ninety degrees with respect to a length of the sensor.

18. The sensor of claim 10, further comprising, encapsulated by the sensor body:
    one or more additional electrical circuits, each connected to a different one of one or more additional signal transmission electrodes; and
    one or more additional mounting substrates, each supporting a different one of the one or more additional electrical circuits and a different one of the one or more additional signal transmission electrodes.

* * * * *